US009345416B2

(12) United States Patent
MacAdam et al.

(10) Patent No.: US 9,345,416 B2
(45) Date of Patent: May 24, 2016

(54) MEANS FOR SECURING A CATHETER INTO A VESSEL

(71) Applicant: Boston Scientific Scimed, Inc., Maple Grove, MN (US)

(72) Inventors: David P. MacAdam, Millbury, MA (US); Charles A. Gibson, Malden, MA (US); Dustin Dufour, Salem, NH (US)

(73) Assignee: Boston Scientific Scimed Inc., Maple Grove, MN (US)

( * ) Notice: Subject to any disclaimer, the term of this patent is extended or adjusted under 35 U.S.C. 154(b) by 0 days.

(21) Appl. No.: 14/192,478

(22) Filed: Feb. 27, 2014

(65) Prior Publication Data

US 2014/0180053 A1    Jun. 26, 2014

Related U.S. Application Data

(63) Continuation of application No. 13/186,192, filed on Jul. 19, 2011, now abandoned.

(60) Provisional application No. 61/386,281, filed on Sep. 24, 2010.

(51) Int. Cl.
*A61B 5/042* (2006.01)
*A61B 5/00* (2006.01)
*A61M 25/04* (2006.01)

(52) U.S. Cl.
CPC .............. *A61B 5/042* (2013.01); *A61B 5/0422* (2013.01); *A61B 5/6853* (2013.01); *A61B 5/6858* (2013.01); *A61M 25/04* (2013.01)

(58) Field of Classification Search
CPC ..... A61B 5/042; A61B 5/0422; A61B 5/6858
USPC .......................................................... 600/381
See application file for complete search history.

(56) References Cited

U.S. PATENT DOCUMENTS

| | | | |
|---|---|---|---|
| 5,221,261 A | | 6/1993 | Termin et al. |
| 5,311,866 A | * | 5/1994 | Kagan et al. .................. 600/374 |
| 5,383,852 A | | 1/1995 | Stevens-Wright |
| 5,462,527 A | | 10/1995 | Stevens et al. |
| 5,611,777 A | | 3/1997 | Bowden et al. |
| 5,846,238 A | | 12/1998 | Jackson et al. |
| 5,860,974 A | * | 1/1999 | Abele .............................. 606/41 |
| 6,004,269 A | * | 12/1999 | Crowley et al. ............... 600/439 |
| 6,917,834 B2 | | 7/2005 | Koblish et al. |
| 7,107,105 B2 | | 9/2006 | Bjorklund et al. |
| 7,218,958 B2 | | 5/2007 | Rashidi |

(Continued)

OTHER PUBLICATIONS

International Search Report and Written Opinion issued in PCT/US2011/044544, mailed Nov. 25, 2011, 9 pages.

*Primary Examiner* — Lee S Cohen
(74) *Attorney, Agent, or Firm* — Faegre Baker Daniels LLP

(57) ABSTRACT

An electrophysiology catheter, e.g., a coronary sinus catheter, for insertion into a cardiac vessel, such as the coronary sinus, includes a handle and a catheter shaft coupled at one end to the handle. The catheter shaft has a distal end and an anchor is associated with the catheter shaft and is movable between a deployed position and a collapsed position. In the deployed position, the anchor extends radially outward from an outer surface of the catheter shaft for contacting a wall and temporarily anchoring the catheter shaft within the coronary sinus. The catheter also includes an actuator for causing deployment and collapsing of the anchor upon manipulation of the actuator.

13 Claims, 10 Drawing Sheets

(56) References Cited

U.S. PATENT DOCUMENTS

| | | |
|---|---|---|
| 7,306,594 B2 | 12/2007 | Collins et al. |
| 7,330,765 B2 | 2/2008 | Haldeman |
| 7,496,394 B2 | 2/2009 | Ahmed et al. |
| 7,722,604 B2 | 5/2010 | Brown et al. |
| 7,727,229 B2 | 6/2010 | He et al. |
| 7,938,826 B2 | 5/2011 | Davis et al. |
| 8,052,731 B2 | 11/2011 | Soltis et al. |
| 8,340,751 B2 * | 12/2012 | Markowitz et al. ........... 600/523 |
| 2002/0087208 A1 | 7/2002 | Koblish et al. |
| 2003/0195507 A1 * | 10/2003 | Stewart et al. ................. 606/41 |
| 2004/0215139 A1 | 10/2004 | Cohen |
| 2005/0065420 A1 | 3/2005 | Collins et al. |
| 2008/0033421 A1 | 2/2008 | Davis et al. |
| 2010/0324552 A1 | 12/2010 | Kauphusman et al. |

\* cited by examiner

MEANS FOR SECURING A CATHETER INTO A VESSEL

CROSS-REFERENCES TO RELATED APPLICATIONS

The present application is a continuation application of U.S. patent application Ser. No. 13/186,192, filed Jul. 19, 2011, now abandoned, which claims priority to U.S. Provisional Patent Application No. 61/386,281, filed Sep. 24, 2010, under 37 C.F.R. §1.78, the complete disclosures of which are incorporated herein by reference.

TECHNICAL FIELD

The present invention relates medical equipment, and in particular, to an electrophysiology catheter, such as a coronary sinus catheter, that includes an actuatable mechanism for anchoring the catheter at a desired location.

BACKGROUND

The human heart is a very complex organ, which relies on both muscle contraction and electrical impulses to function properly. The electrical impulses travel through the heart walls, first through the atria and then the ventricles, causing the corresponding muscle tissue in the atria and ventricles to contract. Thus, the atria contract first, followed by the ventricles. This order is essential for proper functioning of the heart. The coronary sinus is a collection of veins joined together to form a large vessel that collects blood from the myocardium of the heart. It delivers deoxygenated blood to the right atrium in conjunction with the superior and inferior vena cava. The coronary sinus opens into the right atrium, between the inferior vena cava and the auriculo-ventricular opening. It returns the blood from the heart, and is protected by a semicircular fold of the lining membrane of the auricle, the coronary valve.

An indwelling positioned coronary sinus catheter is used as a reference site for electrophysiology studies due to its tubular shape and anatomical positioning on the atrioventricular groove (AV) groove. Catheters are inserted into the coronary sinus ostium and advanced distally to provide both left sided (most distal) and right sided (most proximal) signals. Because the coronary sinus is located in the AV groove, the signals uniquely show both atrial and ventricular activity. The current state of the art CS catheter uses ten (10) poles for recording signals throughout the coronary sinus. Because these catheters are stationary they make a good choice for a timing reference when performing a mapping procedure while a second or third catheter is in the chambers of the heart. They are also used as location or position references with 3D mapping systems such as Velocity™, NAVX™ sold by St. Jude Medical or the CARTO XP and CARTO3 systems sold by BioSense-Webster division of Johnson and Johnson.

Unfortunately, current coronary sinus catheters suffer from a number of disadvantages and in particular, physicians have reported that the coronary sinus catheter can move during the electrophysiology procedure and, when it does, there will be a change in the reference signal. This creates inaccuracies in maps and makes comparisons from one map to another very difficult. There is therefore a need for an improved coronary sinus catheter that overcomes the disadvantages associated with the conventional coronary sinus catheter.

SUMMARY

According to one embodiment, an electrophysiology catheter, such as a coronary sinus catheter, for insertion into a cardiac vessel, such as a coronary sinus, includes a handle and a catheter shaft coupled at one end to the handle. The catheter shaft has a distal end and an anchor is associated with the catheter shaft and is movable between a deployed position and a collapsed position. In the deployed position, the anchor extends radially outward from an outer surface of the catheter shaft for contacting a wall and temporarily anchoring the catheter shaft within the coronary sinus. The catheter also includes an actuator for causing deployment and collapsing of the anchor upon manipulation of the actuator.

The anchor can be in the form of a wire mesh structure and the actuator is operatively coupled to the mesh using a mechanical attachment or link member. The link can be in the form of a flexible elongated mandrel that extends within the catheter shaft and is coupled at one end to the actuator and at an opposite end is connected to a slidable collar that is disposed about the outer surface of the catheter shaft. A proximal end of the wire mesh structure can be fixedly attached to the catheter shaft and a distal end of the wire mesh structure can be attached to a collar such that when the collar moves in a proximal direction, the distal end of the wire mesh structure moves in a proximal direction and the wire mesh structure is deployed by extending radially outward relative to the catheter shaft. Conversely, a distal end of the wire mesh structure can be fixedly attached to the catheter shaft and a proximal end of the wire mesh structure can be attached to the collar such that when the collar moves in a distal direction, the proximal end of the wire mesh structure moves in a distal direction and the wire mesh structure is deployed by extending radially outward relative to the catheter shaft.

The anchor can also be in the form of a plurality of splines that are disposed within an interior of the catheter shaft and project through openings formed in the catheter shaft when in the deployed position. Each spline is disposed within a lumen that is formed within the catheter shaft and the splines are operatively coupled to the actuator such that movement of the actuator is translated into the splines moving between the deployed position in which the splines extend through the openings and extend radially outward from the catheter shaft and the collapsed position in which the splines lie within the lumens.

In yet another embodiment, an electrophysiology catheter, such as a coronary sinus catheter for insertion into a cardiac vessel, such as a coronary sinus, includes a handle and a catheter shaft coupled at one end to the handle. The catheter shaft has a distal end and an inflatable balloon is disposed along an outer surface of the catheter shaft in a location proximal to the distal end. The balloon is inflatable between a deployed position and a collapsed position. In the deployed position, the balloon extends radially outward from the outer surface of the catheter shaft for contacting a wall and temporarily anchoring the catheter shaft within the coronary sinus. The catheter also includes an actuator for causing deployment and collapsing of the anchor upon manipulation of the actuator.

The catheter shaft has an entrance port formed at the distal end that forms an entrance into a conduit that passes within the shaft beneath the inflatable balloon and at least one exit port that is formed proximal to the balloon and in communication with the conduit such that the entrance port is formed on one side of the inflatable balloon and the exit port is formed on the other side of the inflatable balloon. When the inflatable balloon is fully deployed, blood flows into the entrance port through the conduit and out the exit port. The balloon can be ovoid in shape in one implementation.

It will be appreciated that in the various embodiments disclosed herein, the anchoring mechanism does not occlude fluid (e.g., blood) flow within the vessel when the catheter is in the deployed position.

Various arrangements are disclosed that can be combined and still be within the scope of the present disclosure. These and other aspects, features and advantages shall be apparent from the accompanying Drawings and description of certain embodiments of the invention.

DETAILED DESCRIPTION OF CERTAIN EMBODIMENTS OF THE INVENTION

Figure 1:
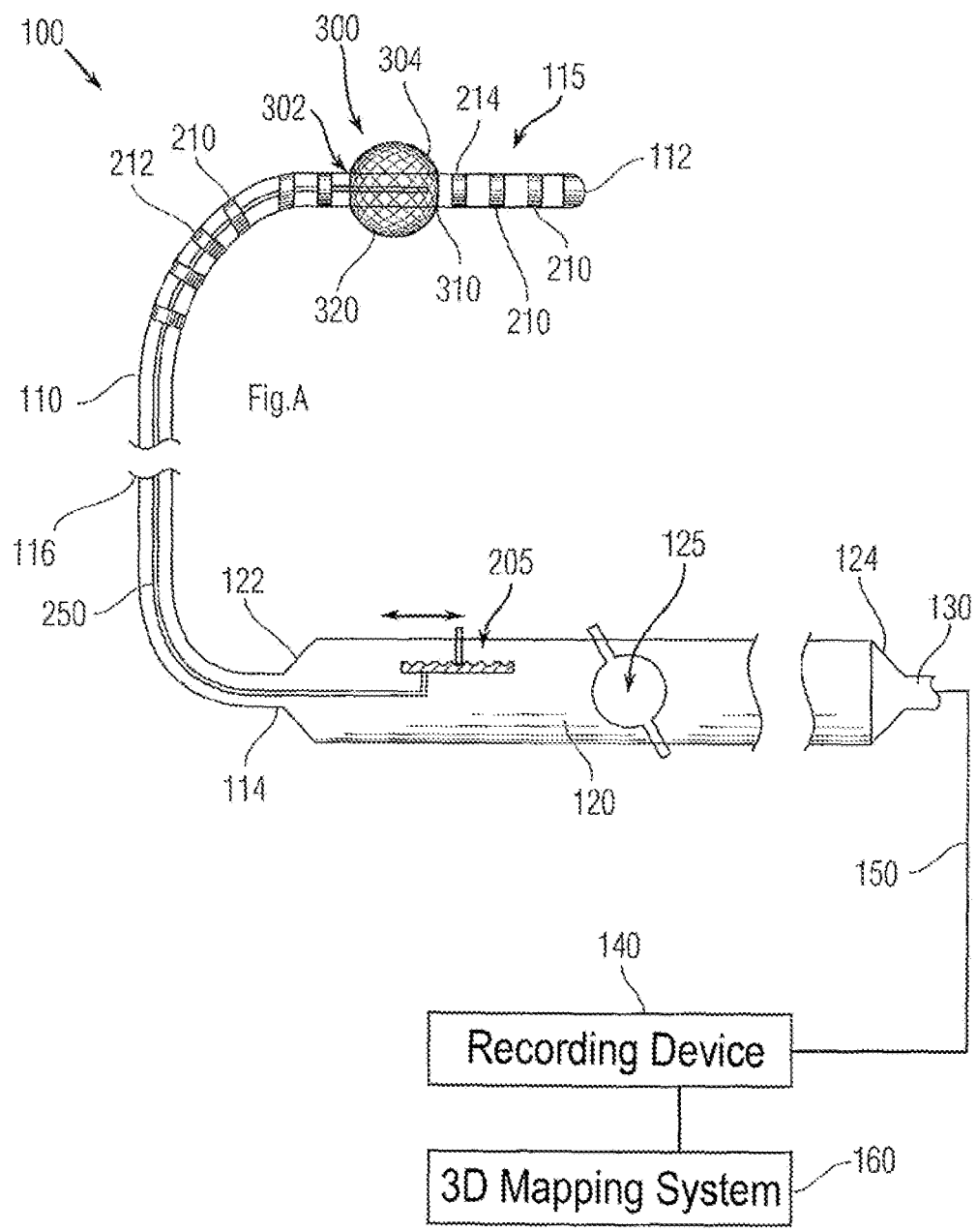
FIG. 1 is a side view of an electrophysiology catheter (e.g., a coronary sinus catheter) with an anchor mechanism according to a first exemplary embodiment of the present invention.
Figure 2:
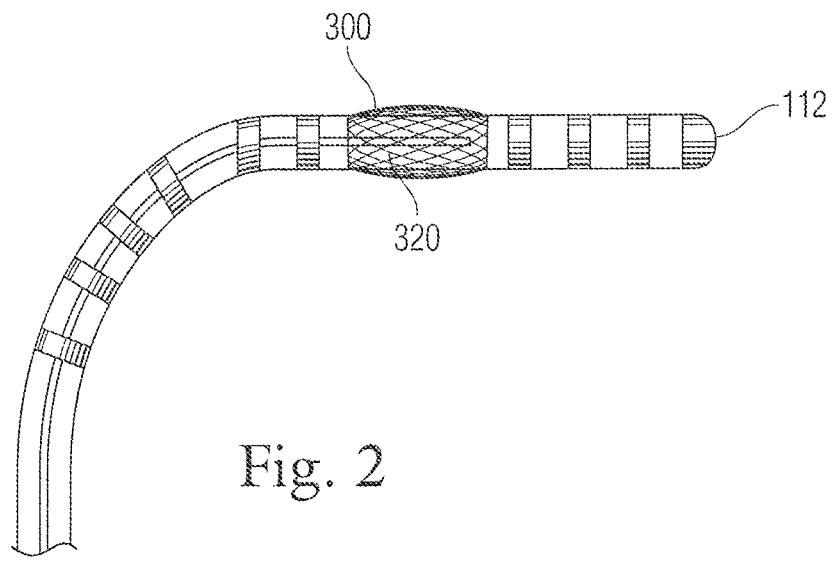
FIG. 2 is a local side view of a distal end of the catheter shaft of the catheter of FIG. 1 showing the anchor in a collapsed position.
Figure 3:
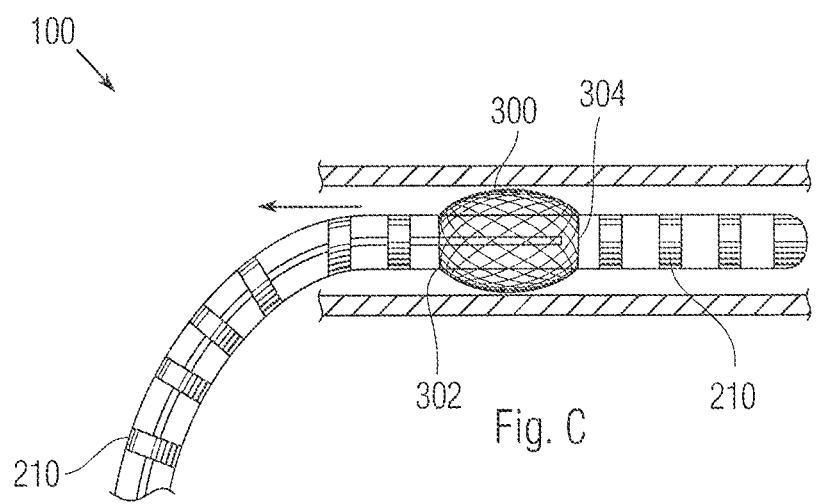
FIG. 3 is a side view of the catheter of FIG. 1 within the coronary sinus with the anchor in a deployed position.

In accordance with a first embodiment of the present invention, shown in FIGS. 1-3, a coronary sinus (CS) catheter 100 is provided. The catheter 100 has a shaft portion 110, a control handle 120 and a connector portion 130. The catheter 100 is preferably part of a catheter system and when the catheter 100 is used in a mapping application, the catheter 100 can be operatively coupled to a recording device 140 via a cable 150 or the like. Signals coming from the catheter 100 can be processed and delivered to the recording device 140. In addition, the catheter system can include and be connected to a 3D mapping system 160.

It will also be understood that the catheter 100 can be part of a catheter system that can include an energy source that is operatively connected to the connector portion 130, as by cable 150, for selectively delivering energy to one more portions of the catheter. It will be appreciated that the energy source and the recording device 140 can be incorporated into a single unit.

As illustrated, the catheter shaft portion 110 includes a distal end 112 and an opposite proximal end 114 that joins the control handle 120. The shaft portion 110 is a hollow structure that includes at least one lumen to allow routing of different members, such as wires, etc., along the length of the shaft portion 110. The catheter shaft portion 110 includes an outer surface 116. As shown in FIG. 1, the distal end 112 includes a distal tip that can have a rounded shape.

Similarly, the control handle 120 includes a first end 122 and an opposing second end 124 with the first end 122 being the end of the control handle 120 that is joined to the shaft portion 110. The second end 124 is the end that joins to the connector portion 130. The control handle 120 can have any number of different shapes and is designed to be held by the operator during the procedure and further can provide accessible control features that permit control and/or operation of the catheter 100.

For example, the catheter 100 can be a steerable device. For example, a distal tip portion 115 of the catheter shaft portion 110 can be deflected by a mechanism that is incorporated within the control handle 120. The control handle 120 can include a rotatable thumbwheel and/or a slide actuator which can be used by a user to deflect the distal end of the catheter. In FIG. 1, a steering mechanism is generally indicated at 125. The thumbwheel (or any other suitable actuating device) is connected to one or more pull or push wires which extend through shaft portion 110 and are connected to the distal end of the catheter at an off-axis location, whereby tension applied to one or more of the pull wires causes the distal portion of the catheter to curve in a predetermined direction or directions. U.S. Pat. Nos. 5,383,852; 5,462,527 and 5,611, 777, which are hereby incorporated by reference in their entirety, illustrate various embodiments of control handle that can be used for steering the catheter 100.

The catheter 100 includes one or more electrodes and preferably includes a plurality of electrodes 210 that are disposed along the length of the shaft portion 110. The electrodes 210 can be in the form of recording electrodes when the catheter 100 is used as part of a mapping application. In the illustrated embodiment, the electrodes 210 are divided into two groups and in particular, the electrodes 210 are divided into a first set 212 of electrodes and a second set 214 of electrodes. The second set 214 of the electrodes are located in the distal tip portion 115 and one of the electrodes in the second set 214 is located at the distal end 112 (a tip electrode). The number of electrodes in the first set 212 can be the same or different than the number of electrodes in the second set 214. When the catheter 100 is used in a mapping application, the electrodes 210 are operably connected to the recording device 140 and/or 3D mapping system 160. As previously mentioned, it is also within the scope of the present invention that the catheter 100 can be used in an ablation application in which case the electrodes 210 are operatively connected to an energy source to allow energy to be delivered to selected electrodes. The electrodes 210 can be in the form of electrode bands.

In accordance with the present invention, the catheter 100 includes a mechanism for anchoring the shaft portion 110 in a desired location (coronary sinus) during the electrophysiology procedure by deployment of an anchor 300. In particular, the mechanism is a user actuatable mechanism that causes the anchor 300 to be either deployed or to be collapsed (return the anchor to a normal operating position). The mechanism includes an actuator 205 that is accessible to the user and is designed so that upon manipulation of the actuator 205, the anchor 300 is either moved to a deployed position or is withdrawn and moved to a collapsed position. The actuator 205 is preferably disposed within the control handle 120; however, other locations are possible for placement of the actuator 205. It will also be appreciated that any number of different types of actuator designs can be used including a slide actuator, a thumbwheel, etc.

In the illustrated embodiment, the actuator 205 is a slide actuator that is slid linearly to cause the anchor 300 to change its position and in particular, to cause the anchor 300 to either deploy or to be placed back into a collapsed position. The slide actuator 205 is operatively coupled to the anchor 300 such that the sliding action of the actuator 205 is translated into a change in the position (condition) of the anchor 300 (e.g., anchor 300 deploys and radially expands so as to provide a structure that anchors the catheter 100 in place, or conversely, anchor 300 radially contracts and is returned to a collapsed state. FIG. 1 shows the anchor 300 in its deployed position and FIG. 2 shows the anchor 300 in its collapsed position.

Any number of different techniques and mechanisms can be used to mechanically couple the actuator 205 to the anchor 300 to cause a translation of the movement of the actuator 205 into the desired radial expansion and radial contraction of the anchor 300. In one embodiment, a mechanical attachment member or link member in the form of a mandrel 250 is coupled to both the anchor 300 and the actuator 205 and is constructed so that it can withstand the normal movements of the catheter 100 including the selected bending of a portion of the catheter shaft 110. For example, the anchor 300 can have a proximal end 302 and an opposing distal end 304 that is closer to the distal end 112 of the catheter shaft 110. The proximal end 302 of the anchor 300 is fixed relative to the catheter shaft 110, while the distal end 304 is an adjustable end in that it can move relative to the catheter shaft 110 or vice versa.

Any number of different members can be used to couple the mandrel 250 to the distal end 304 of the anchor 300 to allow controlled movement of the distal end 304 both relative to the catheter shaft 110 and the proximal end 302. For example, a coupling member 310, such as a slide ring or collar can be used and disposed about the outer surface of the catheter shaft 110. The coupling member 310 is movable relative to the catheter shaft 110 and is coupled to the distal end 304 of the anchor 300 such that movement of the coupling member 310 (due to movement of the mandrel 250) is translated into movement of the anchor 300 in the desired direction.

The coupling member 310 can even travel in one or more channels formed in the outer surface of the catheter shaft 110 to control the movement of the coupling member 310. For example, a pin and groove mechanism can be employed between the coupling member 310 and the catheter shaft 110.

The mandrel 250 can be constructed using methods that are identical or similar to those previously disclosed by the current assignee for a mesh or sliding electrode catheter. For example, see U.S. Pat. No. 7,727,229 and U.S. patent application publication No. 2007/0129717, each of which is hereby incorporated by reference in its entirety. The mandrel 250 can thus be an elongate structure that has one end that is coupled to the coupling member 310 and another end that is coupled to the actuator 205. Alternatively, the catheter shaft 110 can include a dedicated lumen formed therein along at least a length thereof for containing the mandrel 250. In this manner, the mandrel 250 can be both mechanically and electrically isolated from the recording wires and other electrical components that are in communication with the electrodes 210.

In yet another embodiment, the mandrel 250 can be used intentionally as a conductor to carry electrical signals from selected areas of the anchor 300 which in this case can function as a recording electrode. It will further be appreciated that separate electrical wires can be routed to select sections (e.g., wires) of the anchor 300 (e.g., a wire mesh) to facilitate recording signals.

In the illustrated embodiment, the anchor 300 is located between the first set of electrodes 212 and the second set of electrodes 214; however, this is merely one exemplary location for the anchor 300 and the anchor 300 can thus be located anywhere along the catheter shaft 110 that allows the anchor 300 to perform the intended function. Typically, the anchor 300 will be located adjacent or proximate electrodes since anchoring of the catheter shaft 110 is desirable in the region where electrodes are present to permit the electrodes to perform their intended function. In the case of a coronary sinus catheter, the electrodes are recording electrodes. However, in other catheter designs, the electrodes 210 can be constructed specially as mapping or ablation electrodes. Depending upon the application, electrodes 210 are optimally placed relative to the location of the anchor 300 and typically, as previously mentioned, electrodes are located both proximal and distal to the anchor 300.

The anchor 300 can take any number of different forms so long as the structure can be deployed and collapsed relative to the catheter shaft and permits conventional catheter functions and operations to be performed. In particular, since the anchor 300 is designed to hold the catheter shaft 110 in place within a vessel (e.g., coronary sinus), the anchor arrangement cannot obstruct fluid flow (e.g., blood flow) within the vessel. In one embodiment, the anchor 300 is in the form of a mesh structure, such as a braided mesh structure, that is disposed about the outer surface of the catheter shaft 110 and can be moved between both collapsed and deployed positions, as previously described. It will also be appreciated that the anchor 300 can be locked in positions that are between the fully collapsed position and the fully deployed position.

The anchor 300 can thus be in the form of a plurality of interlaced filaments 320, such as wires that form a braided wire mesh. The filaments are flexible and capable of being expanded radially outwardly from catheter shaft 110. The filaments 320 can be formed of metallic elements having relatively small cross sectional diameters, such that the filaments can be expanded radially outwardly. The filaments may be round, having a dimension on the order of about 0.001-0.030 inches in diameter. Alternatively, the filaments may be flat, having a thickness on the order of about 0.001-0.030 inches, and a width on the order of about 0.001-0.030 inches. The filaments can be formed of Nitinol type wire. Alternatively, the filaments may include non-metallic elements, or non-metallic elements woven with metallic elements, with the non-metallic elements providing support to or separation of the metallic elements. A multiplicity of individual filaments 320 can be provided in braided mesh structure 300, for example up to 300 or more filaments 320. It will be appreciated that the aforementioned dimensions and description is merely exemplary for a mesh structure according to one embodiment and other structures and other dimensions are equally possible so long as the intended catheter functions and operations can be performed.

As mentioned herein, in some embodiments, the anchor 300 can be formed of wire filaments (wires) and the filaments 320 can be electrically isolated from each other by an insulation coating. This insulation coating may be, for example, a polyimide type material. A portion of the insulation on the outer circumferential surface of the braided conductive member is removed. This allows each of the filaments to facilitate recording signals. Alternatively, specific filaments 320 can be permitted to contact each other to form a preselected grouping of filaments 320.

Each of the filaments 320 can be helically wound under compression about the catheter shaft 110. As a result of this helical construction, select movement of the anchor 300 causes radial expansion of the anchor 300 and in particular, the radial expansion of the portions of filaments 320 that results in the deployment of the anchor 300.

As mentioned herein, proximal end 302 of the braided wire mesh 300 can be fixed relative to the catheter shaft 110 while the distal end 304 of the braided wire mesh 300 is attached to the sliding coupling member 310. When the coupling member 310 is moved in a proximal direction, the distal end 304 of the wire mesh 300 is drawn towards the proximal end 302 and this results in a radial expansion of the wire mesh 300. The coupling member 310 is moved proximally due to proximal movement of the mandrel 250 within the catheter shaft 110. (The converse arrangement can have the mesh expand by moving the coupling member in a distal direction).

When the anchor 300 is positioned between two sets of electrodes, the sets of electrodes are placed to allow for movement of the anchor 300 between the collapsed and deployed positions. In the collapsed position, the distal end 304 of the anchor 300 is closest to the more distally located electrodes (e.g., the second set 214 of electrodes) and when the anchor 300 is deployed, the spacing between the distal end 304 of the anchor 300 and the electrode set is greater. The wire mesh structure of the anchor 300 permits fluid to flow therethrough and thus, when the catheter 100 is placed in a vessel (e.g., the coronary sinus), fluid (e.g., blood) can flow through the wire mesh and its flow is not obstructed as it flows about the catheter 100.

Now referring to FIGS. 1-3, a method of using the catheter 100 as a coronary sinus catheter and for advancing the catheter 100 within the coronary sinus are described. The catheter 100 is advanced by inserting the distal end 112 of the catheter shaft 110 into the coronary sinus (vessel) while the anchor 300 is in the collapsed position as shown in FIG. 2. Once the catheter 100 is in an optimal location within the coronary sinus, the anchor 300 is deployed by manipulating the actuator 205 to cause the mandrel 250 to move in a proximal direction, thereby causing the coupling member 310 to likewise move in a proximal direction. This movement of the mandrel 250 and the coupling member 310 is directly translated into the radial expansion of the anchor 300. FIG. 3 shows the anchor 300 in a deployed position within the coronary sinus.

As discussed herein, the anchor 300 is designed to locate and hold the catheter 100 in its desired location within the coronary sinus by applying outward radial pressure to the vessel wall. Blood flows past the deployed wire mesh 300 due to its open wire construction. The deployment mechanism can be reversed in the design to optimize contact and safe deployment and collapse. This can be achieved by reversing the anchor point from the proximal end 302 to the distal end 304 and attaching the mandrel actuation mechanism to the proximal end 302. In this configuration, a push on the mandrel 250 deploys the wire mesh 300 (anchor) and collapse the wire mesh 300 against the catheter shaft 110.

The actuator 205 also preferably includes a lock mechanism that permits the actuator 205 to be locked in place and prevent inadvertent movement of the anchor 300. For example, when the anchor 300 is fully deployed to position and retain the catheter 100 in its desired position, the actuator 205 can be locked to prevent inadvertent movement of the catheter 100 due to a change in the deployment status of the anchor 300. Similarly, the actuator 205 can be placed into a locked position when the anchor 300 is not deployed (collapsed state).

In one other embodiment, the catheter shaft 110 can be constructed such that when the coupling member 310 is moved to cause the radial expansion of the anchor 300, an electrode (e.g., a ring electrode, etc.) is exposed.

Figure 4:
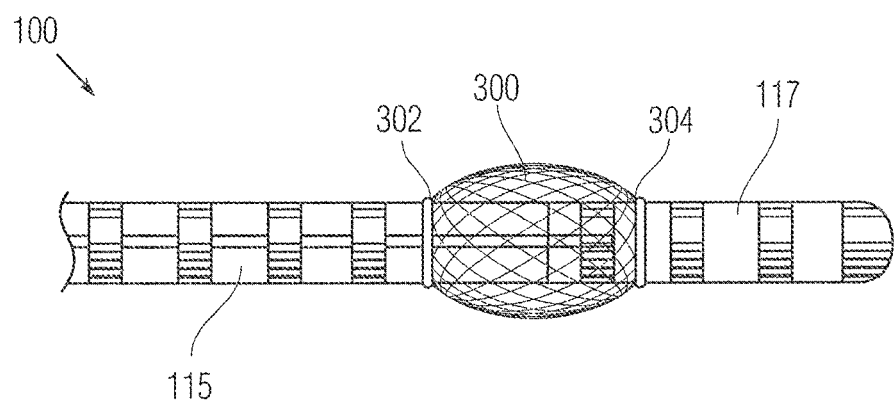
FIG. 4 is a side view of an electrophysiology catheter (e.g., a coronary sinus catheter) with an anchor mechanism according to a second exemplary embodiment of the present invention.

In yet another embodiment that is illustrated in FIG. 4, a telescoping catheter shaft design can be used for deploying and collapsing the anchor 300. In this embodiment, the catheter shaft 110 includes a first main section 115 and a second sliding section 117 that is coupled to the main section 115 and slidable relative thereto. The second sliding section 117 represents the distal end section of the catheter 100 and is disposed relative to the main section 115 so that the sliding section 117 can be moved relative to the main section 115 in both proximal and distal directions. In FIG. 4, the sliding section 117 is disposed about a portion of the outer surface of the main section 115. The sliding section 117 is coupled to the mandrel 250 (not shown) so that movement of the mandrel 250 in the proximal and distal directions is translated into proximal and distal movement of the sliding section 117.

The proximal end 302 of the anchor 300 (e.g., a wire mesh) is fixedly attached to the first main section 115 of the catheter shaft 110, while the distal end 304 of the anchor 300 is fixedly attached to the sliding section 117. When the sliding catheter section 117 is moved in a proximal direction, the anchor 300 is deployed (expands radially outward). Conversely, when the sliding catheter section 117 is moved in a distal direction, the anchor 300 is collapsed due to the flattening out of the anchor 300 along the catheter shaft 110.

In this embodiment, the catheter shaft 110 is thus formed of two sections with one movable relative to the other one to cause a change in the position of the anchor 300.

Figure 5:
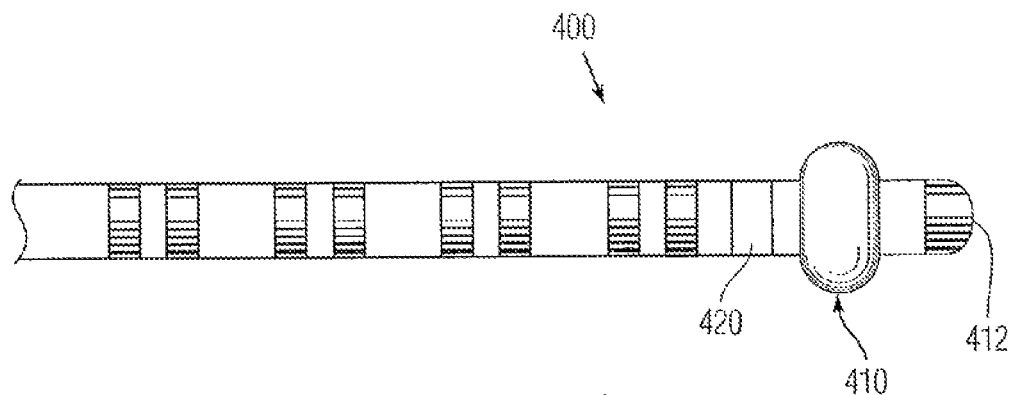
FIG. 5 is a side view of an electrophysiology catheter (e.g., a coronary sinus catheter) with an anchor mechanism according to a third exemplary embodiment of the present invention.
Figure 6:
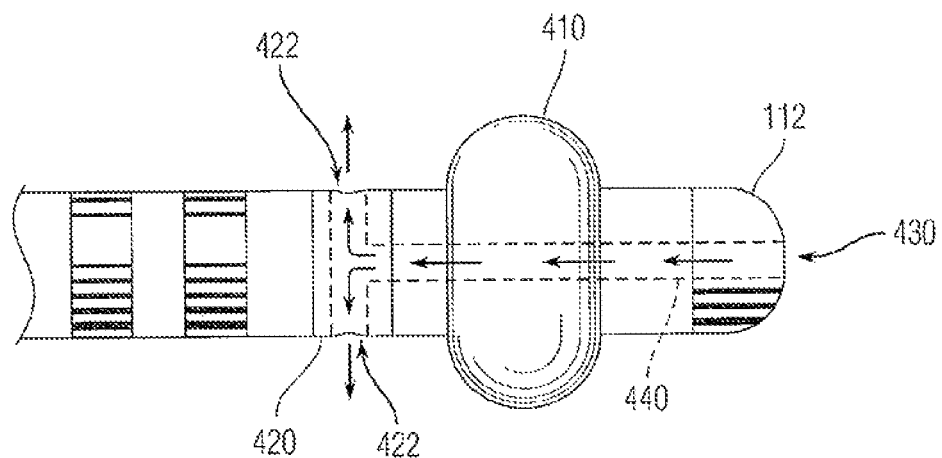
FIG. 6 is a local side view of the catheter shaft of the catheter of FIG. 5 showing blood flow when the distal anchor is deployed.
Figure 7:
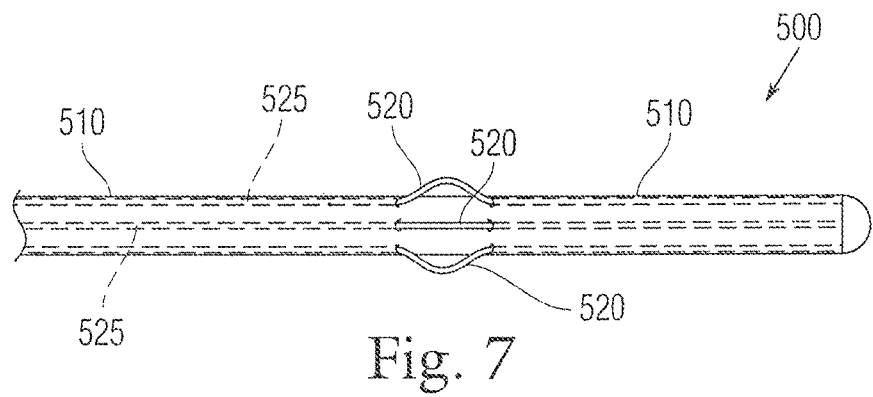
FIG. 7 is a side view of an electrophysiology catheter (e.g., a coronary sinus catheter) with an anchor mechanism according to a fourth exemplary embodiment of the present invention.
Figure 8:
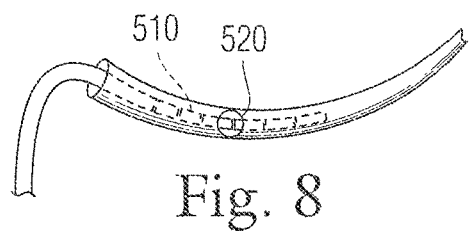
FIG. 8 is a side view of the catheter of FIG. 7 in the coronary sinus with the distal anchor deployed.

Now referring to FIGS. 5 and 6, another mechanism for temporarily anchoring or fixing a catheter 400 within a vessel, such as a coronary sinus, is shown. The catheter 400 is similar to catheter 100 and therefore like elements are numbered alike. The catheter shaft 100 includes a distal tip at the distal end 112. The distal tip can be in the form of a recording electrode or the distal tip can be free of a recording electrode. Proximal to the distal tip 112 is an anchor in the form of an inflatable balloon 410, such as an inflation balloon, that can be inflated so as to extend radially outward from the catheter shaft 110. As described herein the inflation balloon 410 can have any number of different shapes and can have any number of different sizes. One preferred shape is ovoid. The inflation balloon 410 can be inflated using conventional techniques including delivering a fluid, including a liquid or gas, to the inflation balloon 410 using a fluid conduit (e.g., a lumen formed in the catheter shaft) or the like that is routed internally through the catheter shaft and is in communication with the interior of the balloon 410. The inflation of the balloon 410 can be preferably accomplished using controls that are part of the control handle 120 or alternatively, an actuator that is either a part of or separate from the catheter can be used. For example, a syringe or the like or other type of device that holds a fluid can be used to inject fluid into the balloon 410 as by injecting the fluid within one or more inflation lumens that are formed in the catheter shaft and in fluid communication with the interior of the balloon 410. The actuator of the present invention can thus be thought of as any mechanism that is configured to cause the anchor to deploy and/or collapse.

Proximal to the inflation balloon 410, a first port hub 420 is formed in the catheter shaft 110 and in addition, proximal to the inflation balloon 410, recording electrodes 210 are disposed along the length of the catheter shaft 110. The catheter shaft 110 includes an entrance port 430 at the distal tip 112 of the catheter shaft 110 from which a conduit 440, such as a shunt tube, runs through the center of the inflation balloon 410, within the catheter shaft, to the proximal port hub 420. In the proximal port hub 420, there are 1 or more exit ports 422 that are in communication with the entrance port 430 via the shunt tube 430. It will further be appreciated that in some embodiments, the shunt tube 430 can be eliminated due to the construction of the balloon itself, such as when an ovoid shaped balloon is used or a balloon with a non-occluding shape is used.

As with the previous embodiments, the catheter 400 typically includes a steering mechanism and in particular, the catheter 400 can include one or more catheter steering cables (not shown) that can or cannot be anchored to the port hub 420, or the steering cables can pass through the hub 420 to anchor at the distal tip 112.

As with the other embodiments and in contrast to conventional designs, the catheter 400 of the present invention includes a mechanism for temporarily anchoring itself within the vessel (e.g., coronary sinus). The catheter 400 can thus be used as a common coronary sinus diagnostic catheter. Once inserted into the coronary sinus, the inflation balloon 410 is inflated using conventional techniques such as filling the balloon 410 with a fluid or air. The inflation of the balloon 410 results in the catheter 400 being anchored within the coronary sinus in a desired position for added stability and to help prevent the catheter 400 from popping out or otherwise moving within the coronary sinus.

Since blood flows through the coronary sinus, the catheter 400 is designed to accommodate such blood flow. More specifically, blood is allowed to bypass the inflation balloon 410 by first flowing through the entrance port 430 and flowing through the shunt tube 440 to the one or more exit ports 422 through which the blood exits the catheter shaft 110. FIG. 6 shows the flow of blood within the catheter shaft 110. Since the shunt tube 440 runs through the inflation balloon 410, within the shaft, blood can flow in an unimpeded manner even when the inflation balloon 410 is fully inflated and in contact with the walls of the coronary sinus.

Now referring to FIGS. 7-11, another embodiment of the present invention is illustrated for temporarily securing a catheter 500 within a vessel, such as the coronary sinus. The catheter 500 is similar to the other catheters disclosed herein and therefore, like elements are numbered alike. The catheter 500 includes an elongated catheter shaft 510. As with the other embodiments, the catheter 500 has both a deployed state for temporarily securing and holding the catheter 500 in a desired position and location within the vessel (e.g., coronary sinus) and a collapsed state. In this embodiment, the catheter 500 includes a plurality of deployable splines 520. As shown in the figures, when the splines 520 are deployed, the splines 520 move radially outward from the catheter shaft 510 for intimately contacting the walls of the vessel.

In one embodiment, each spline 520 is disposed within a lumen 525 that extends along a length of the catheter shaft 510. In the illustrated embodiment, there are four lumens 525 that contain four splines 520 (e.g., the lumens and splines can be oriented 90 degrees relative to one another). A length of each lumen 525 is exposed along the outer surface of the catheter shaft 110. In other words, the splines 520 are accessible within these exposed lumen sections which can be thought of as being windows 522 formed along the catheter shaft 510. These openings or windows 522 formed within and along the catheter shaft 510 permit the radial expansion (outward radial movement) of the splines 520 and this translates into the splines 520 being moved into contact with the vessel wall (i.e., wall of the coronary sinus).

Figure 10:
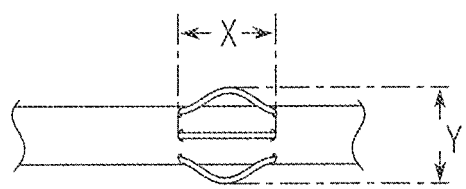
FIG. 10 is side view showing the two dimensions of the anchor.
Figure 11:
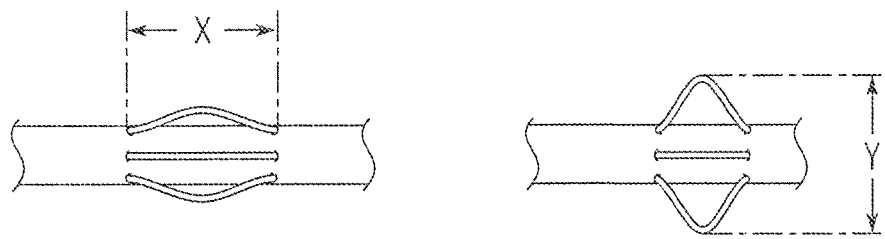
FIG. 11 shows methods of increasing the projection of the anchor elements.
Figure 9:
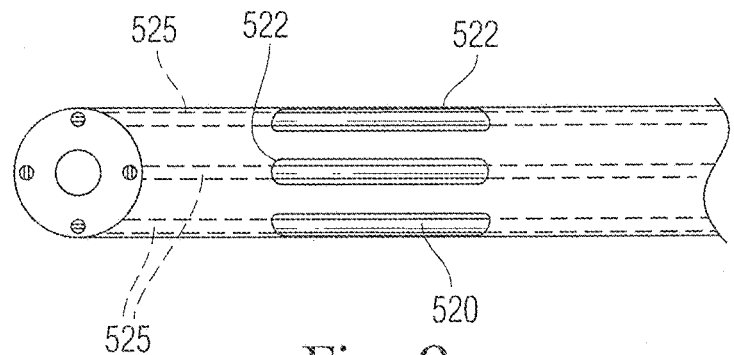
FIG. 9 is an end and side view of the catheter of FIG. 7 showing windows through which anchor elements are deployed.

The location of the splines 520 can vary to coincide with the vessel dimensions and it will be appreciated that the use of splines 520 allows for blood flow to only be minimally restricted (an important consideration in typical coronary sinus applications). The amount of the projection (radial outward movement-diameters) of the spline 520 can be varied by lengthening the degree of exposure of the splines 520 (e.g., increase the length of the window formed within the catheter shaft 510) and/or lengthening the stroke of the exposed splines 520. This is generally shown in FIGS. 10-11, where x is equal to the length of the exposed spline 520 (variable radius or the catheter) and y is equal to the stroke of the spline 520 (e.g., the amount of projection). By altering one or more of these parameters, the overall diameter of the catheter shaft 510 can be varied.

Varying the "y" dimension can be achieved using a number of different mechanisms including a push/pull deployment mechanism to control the spline deployment or spline retraction (collapse).

The splines 520 can be actuated using any number of different techniques where movement of one member, such as an actuator in the handle control section, is translated into the splines 520 either being deployed by expanding radially outward from the catheter shaft or collapsing as by laying flat within the lumens 525. For example, a handle mechanism can be used and include a control in which the splines 520 can be moved forward and rearward within the catheter shaft 510 to cause the deployment and/or collapse of the splines 520. The handle mechanism thus can drive the movement of the splines 520. A dual control handle can be provided if steering is needed as previously described herein.

The splines 520 can be in form of an elongated filament, such as an elongated wire, that is disposed within the lumen 525. However, other materials can be used so long as the splines 520 can be deployed and placed into a collapsed position.

Figure 12:
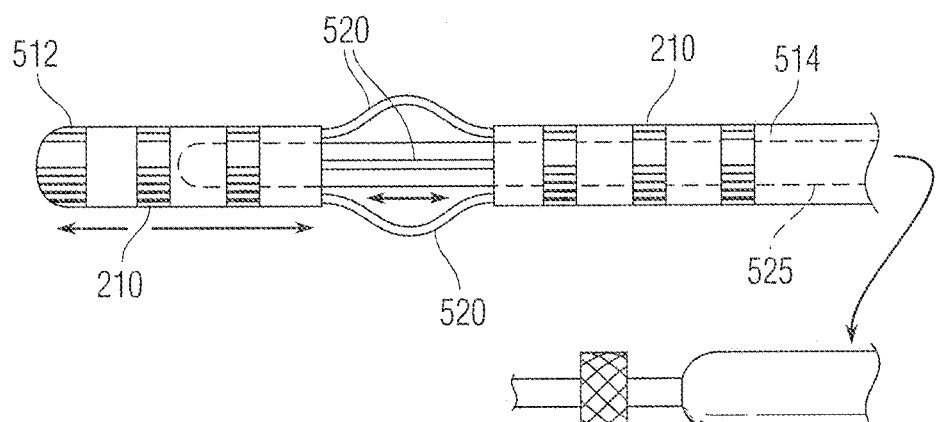
FIG. 12 is a side view of an electrophysiology catheter (e.g., a coronary sinus catheter) with an anchor mechanism according to a fifth exemplary embodiment of the present invention.

FIG. 12 shows an alternative embodiment where the catheter shaft 510 includes a distal end section 512 that is slidable relative to a main shaft section 514. In this embodiment, one end of the spline 520 is attached to the slidable end section 512, while the other end of the spline 520 is attached to the main section 514. As a result, movement of the end section 512 relative to the main section 514 causes a change in the position of the spines 520. For example, the proximal movement of the end section 512 relative to the main section 514 can cause the splines 520 to project radially outward and into contact with the vessel wall for locally anchoring the catheter 500 within the vessel (e.g., coronary sinus). Alternatively, a pushing (movement of the main section 512 relative to the end section 514) can cause deployment of the splines 520. The actuation (deployment) of the splines 520 can be controlled at the control handle portion of the catheter 500. In this embodiment, the catheter shaft 510 can be thought of as being of a telescoping type.

The splines 520 can be actuated using any number of different techniques where movement of one member, such as an actuator in the handle control section, is translated into the splines 520 either being deployed by expanding radially outward from the catheter shaft or collapsing as by laying flat within the lumens 525.

The splines 520 can be in form of an elongated filament, such as an elongated wire, that is disposed within the lumen 525.

Figure 13:
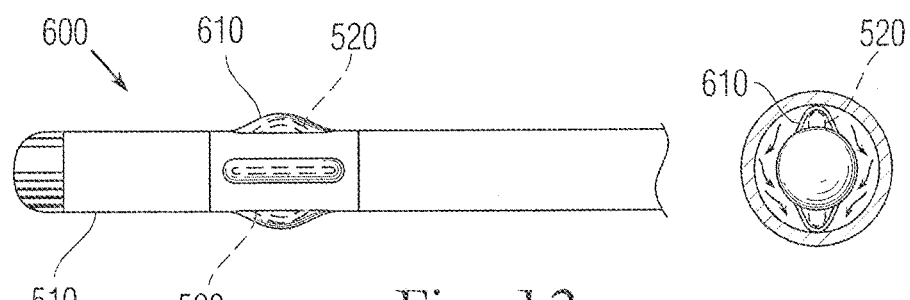
FIG. 13 illustrates side and end views of an electrophysiology catheter (e.g., a coronary sinus catheter) catheter with an anchor mechanism according to a sixth exemplary embodiment of the present invention.

In yet another embodiment, as shown in FIG. 13, a catheter 600 is provided and is similar to the other embodiments disclosed herein with the exception that each spline 520 is covered with a membrane 610 that can readily flex and contract as a result of the movement of the underlying spline 520. The flexible membrane 610 is disposed over a respective spline 520 and is deployed by the spline 520 as shown in the end view of FIG. 13. FIG. 13 shows blood flow around the catheter 600 and shows how the splines 520 anchor and hold the catheter 600 in place within the vessel (e.g., coronary sinus).

The advantages of this embodiment are that this design prevents exposed splines 520 and thus avoids any issues that are attributable to having exposed splines 520 present. At the same time, blood flow is still permitted in the embodiment where the splines 520 lie in a single plane as is the case when the splines 520 are oriented 180 degrees apart. The splines 520 can be a metal, a plastic, etc., and can be flat wire, round wire, etc.

Figure 14:
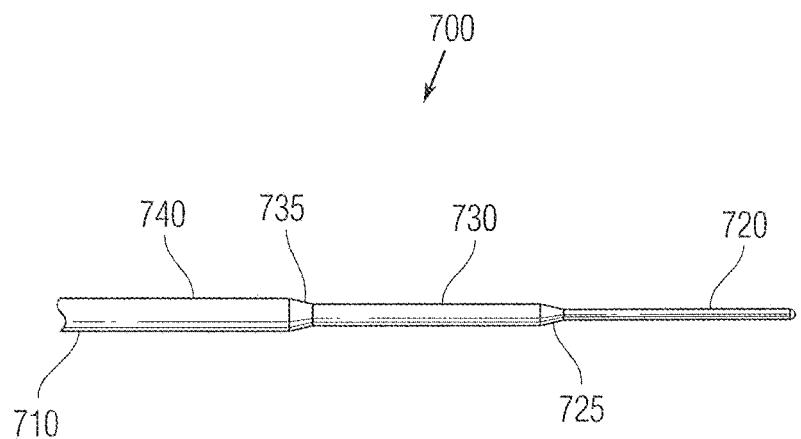
FIG. 14 is a side view of an electrophysiology catheter (e.g., a coronary sinus catheter) with a tapered shaft according to an exemplary embodiment of the present invention.
Figure 15:
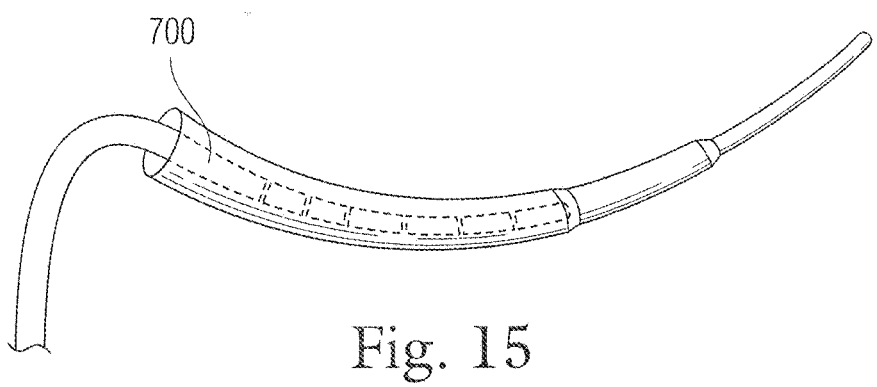
FIG. 15 is a side view of the catheter of FIG. 14 inserted into the coronary sinus.

Now referring to FIGS. 14-15, a catheter 700 according to another embodiment is shown. The catheter 700 is of a tapered design in that a shaft 710 of the catheter 700 has a tapered construction. In the illustrated embodiment, the catheter shaft 710 has three distinct regions, namely, a first region 720, a second region 730, and a third region 740. The first region 720 represents a distal end (distal tip) of the catheter shaft 710 and the third region 740 is the most proximal region with the second region 730 being located between the first and third regions 720, 740. A first taper 725 is formed between the first and second regions 720, 730 and a second taper 735 is formed between the second and third regions 730, 740. The dimensions of the catheter shaft 700 decrease along its length from the proximal end to the distal end and in particular, the first region 720 has the smallest diameter, the third region 740 has the largest diameter and the second region 730 has diameter between the first and third regions 720, 740.

A tapered tip (e.g., two or more tapered regions) facilitates a closer geometry match to the coronary sinus morphology as the surgeon spans the right to left side of the heart during the procedure. In other words, the coronary sinus is typically not of a constant diameter and is better described as having a tapered construction itself. The catheter shaft 710 thus provides the benefit of deeper coronary sinus penetration. A tapered profile can also provide a means to secure the device within the vessel (e.g., coronary sinus). More specifically, the larger diameter portion (e.g., third region 740) of the catheter shaft 710 can become slightly wedged in the coronary sinus as the larger diameter region of the catheter shaft meets a narrower transition within the coronary sinus (vessel).

Figure 16:
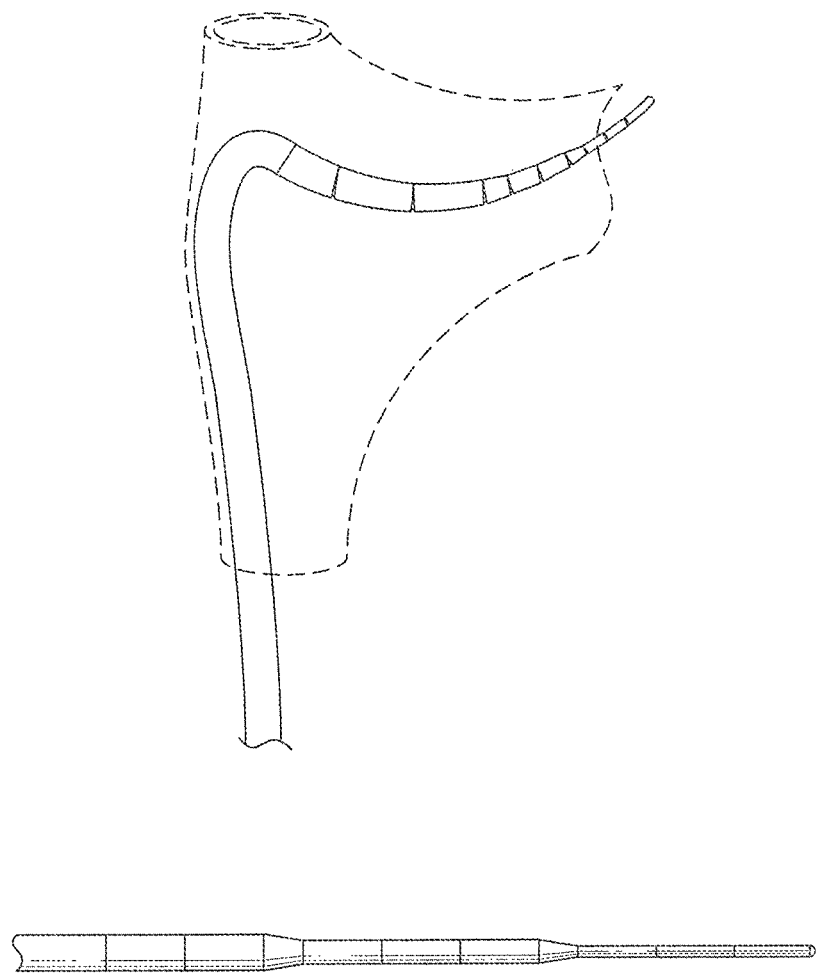
FIG. 16 shows a tapered tipstock used in combination with a conventional proximal shaft.
Figure 17:
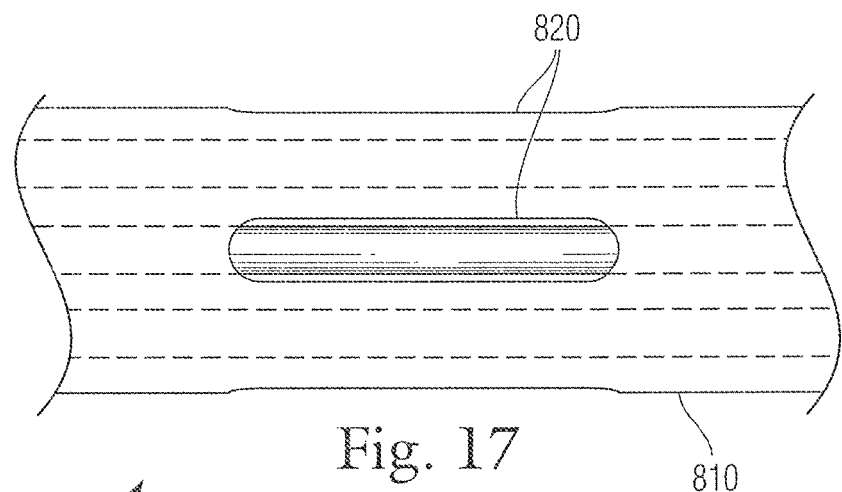
FIG. 17 is a side view of an electrophysiology catheter (e.g., a coronary sinus catheter) with an anchor mechanism according to another embodiment of the present invention.

A tapered transition allows for the ability to maintain an existing transition relationship with a shaft that mates with the larger proximal end, which aides in processing and mechanical properties for traversing the coronary sinus with a strengthened proximal segment. Proximal support of the curve is better for advancement into the coronary sinus versus a device that fails to include the tapered section. FIG. 16 shows a tapered tip stock in the form of the tapered tip of the present invention used in combination with a conventional catheter shaft that has a uniform diameter.

It will be appreciated that the coronary sinus catheter shaft can include a combination of the above described features, including but not limited to the inclusion of an anchor in a distal region of a catheter shaft that has a tapered construction as described herein. In some applications the inclusion of an anchor (e.g., deployable mesh, deployably splines, inflatable balloon, etc.) along a tapered catheter shaft can provide improved results in that the tapered shaft permits the catheter to be disposed further within the coronary sinus and allow deployment of the anchor at an optimal location to anchor the entire catheter. It will also be appreciated that it is also within the scope of the invention that two different anchors (of same type or different types) can be utilized.

Figure 18:
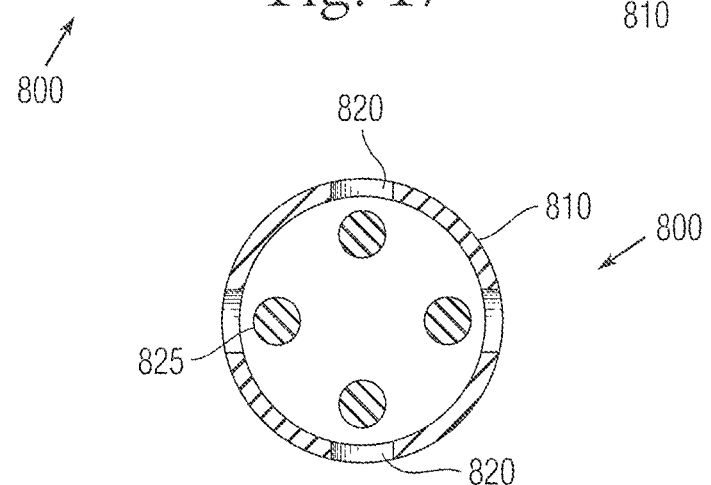
FIG. 18 is a cross-sectional view of an anchor mechanism in a collapsed state.
Figure 19:
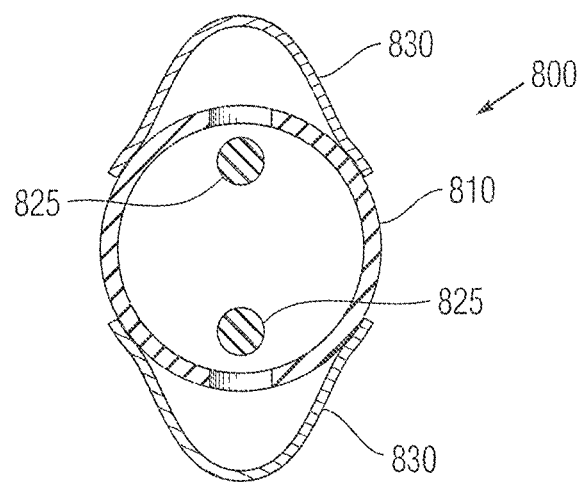
FIG. 19 is a cross-sectional view of an anchor mechanism in a deployed state.
Figure 20:
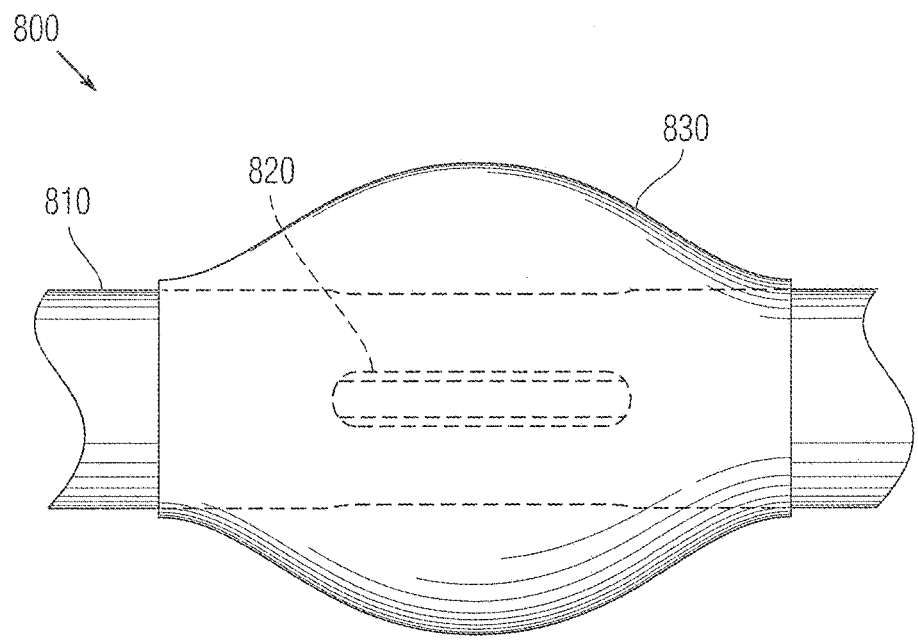
FIG. 20 is side view of the anchor mechanism in the deployed state.

FIGS. 17-21 illustrate an electrophysiology catheter (e.g., coronary sinus catheter) 800 according to another embodiment. The catheter 800 includes an elongated shaft 810 similar to the other catheters disclosed herein. It will be understood that the catheter 800 can include the same features of the catheter 100 shown in FIG. 1 including one or more control mechanisms that are part of a handle, etc. and can be operatively connected to other equipment, such as the recording device 140 and/or the 3D mapping system 160. For ease of illustration, FIGS. 17-21 only show a portion of the catheter shaft 810. The catheter shaft 810 can be of a single lumen type or of a multi lumen type. FIGS. 17-21 illustrate a multi lumen type. In accordance with the invention, the catheter shaft 810 has one or more (preferably two or more) windows 820 formed in the catheter shaft 810. The windows 820 can be elongated slots formed in the shaft 810. FIG. 18 shows four windows 820 and FIG. 19 shows two windows 820. The windows 820 are preferably formed opposite (180 degrees one another since this permits the anchor to contact the vessel in two opposite points (locations); however, they can be located in positions that are not directly opposite one another.

Each window 820 of the catheter shaft 810 is in fluid communication with at least one lumen 825 that is formed in the shaft 810. Each window 820 can have its on respective lumen 825 formed in the catheter shaft in which case each window 820 is in fluid communication with a respective lumen 825 or one lumen 825 can be in communication with two or more windows 820.

An inflatable member 830 is disposed about the catheter shaft 810 in covering relation to the windows 820. In other words, the inflatable member 830 covers the windows 820. In one embodiment, the inflatable member 830 is a balloon, such as an ovoid shaped balloon that is disposed about the shaft 810. In this embodiment, the balloon is a continuous structure about the outer surface of the catheter shaft. However, it will also be appreciated that the inflatable member 830 can be formed of one or more sections of flexible material that expands when a fluid force is applied thereto and collapses when the fluid force is removed. In other words, each window 820 can be covered with a single piece or section of a material that has inflatable characteristics (e.g., balloon like material) and the regions between the windows 820 can be entirely free of the expandable material. In this embodiment, the pieces of expandable material are bonded or otherwise attached to the outer surface of the catheter shaft along the periphery of the respective window 820.

Figure 21:
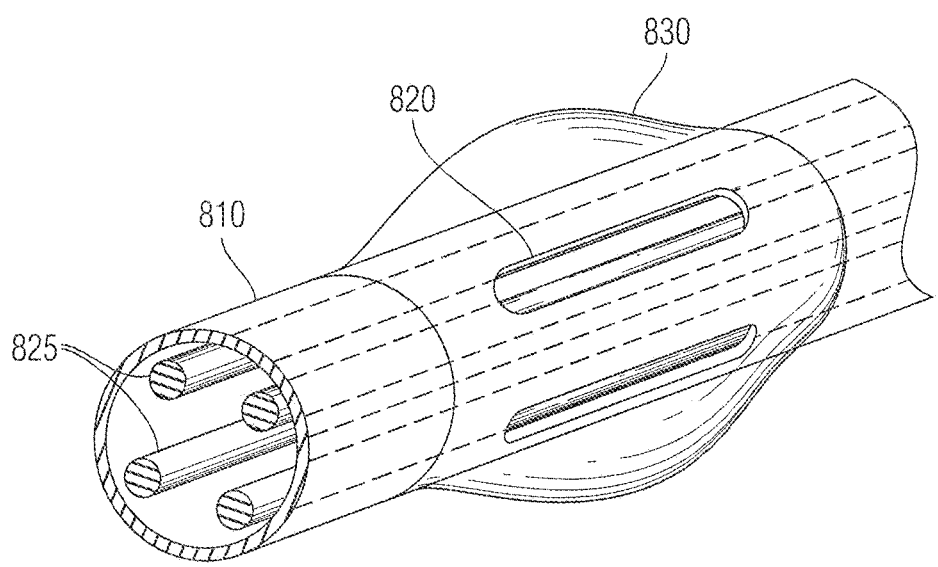
FIG. 21 is a perspective view of the catheter of FIG. 18.

When an inflation fluid, such as a gas (air) or liquid, flows through the lumen(s) 825, the fluid flows through the window(s) that is fluidly connected to the lumen and into the inflatable member 830 for inflation thereof. Alternatively, in the embodiment where sections or pieces of material are individually disposed over each window or the embodiment where the balloon is bonded to the catheter shaft in regions between the catheter shaft, the fluid force of the fluid flowing through the window against the piece of material causes the radial expansion of the material locally above the window. For example, the inflatable member 830 is at least locally inflated in the areas of the windows 820. This is shown in FIGS. 18 and 19. As shown in FIG. 21, the inflatable member 830 can be bonded or otherwise secured to the catheter shaft 810 in areas surrounding the windows 820 so as to prevent inflation of the member 830 in areas that are not overlying a window 820. As a result, the inflation characteristics are influenced and controlled by the shape of the window 820 and in the case of two or four windows, the resulting inflated structure can be thought of as being two or four elongated inflated sections (i.e., balloon splines) that overlie the window 820.

It will be understood that the fluid (e.g., blood) can flow around the balloon splines and thus, fluid flow (e.g., blood flow) is not occluded. In other words, in regions where the inflatable member 830 is bonded to the catheter shaft 810 or in regions of the shaft 810 where the inflatable member 830 is absent, fluid flows freely along the catheter shaft 810 since the balloon splines are absent in these regions.

As with the other embodiments, the catheter 800 can be a coronary sinus catheter that is used in the coronary sinus.

In addition, it will be appreciated that the catheters described herein are configured so that the anchor element can be partially deployed in that it can be deployed in a position between the fully collapsed position and the fully deployed position. Partial deployment may be desired in a narrower coronary sinus, etc. Partial deployment is possible in both the mechanically actuated anchor structures, such as the mesh, splines, etc., as well as the embodiments where the anchor is an inflatable member, such as a balloon in which case the balloon is only partially inflated.

Example

In accordance with the present invention, a catheter according to one of the embodiments is inserted into the coronary sinus by first inserting a distal end of the catheter into the coronary sinus. The catheter is inserted with the anchor being in a collapsed position or state. The catheter is continually advanced within the coronary sinus and the position of the catheter can be monitored until the catheter is in a target area of the coronary sinus. When the catheter is being used as part of a mapping application, the target area can be a location where the mapping electrodes of the catheter are in locations where mapping signals are to be detected. Once the catheter is in a desired location within the coronary sinus where a mapping application is to be performed, the anchor is then deployed. In its deployed position, the anchor locally anchors the catheter within the coronary vessel by applying a radially outward force against the vessel wall. However, as discussed herein, the embodiments of the present invention do not occlude blood flow and therefore, blood flows around the deployed anchor. Once the mapping application is completed, the anchor can then be collapsed and the catheter is moved in the opposite direction resulting in the catheter shaft being removed from the coronary sinus.

While the invention has been described in connection with certain embodiments thereof, the invention is capable of being practiced in other forms and using other materials and structures. In particular, features of different embodiments can be combined, for example, to have splines or covered splines on a taper-tipped catheter, and so on. Accordingly, the invention is defined by the recitations in the claims appended hereto and equivalents thereof.

What is claimed is:

1. An electrophysiology catheter for insertion into a cardiac vessel comprising:
   a handle;
   a catheter shaft coupled at one end to the handle;
   an anchor comprising:
      a plurality of wires arrayed around the catheter shaft; and
      a collar disposed around the catheter shaft and slideable along the catheter shaft, the collar attached to a first end of each of the plurality of wires,
      wherein the plurality of wires are movable between a deployed position and a collapsed position based on movement of the collar relative to the catheter shaft,
      wherein in the deployed position, the plurality of wires extend radially outward from an outer surface of the catheter shaft for contacting a wall of the cardiac vessel and temporarily anchoring the electrophysiology catheter shaft within the cardiac vessel while permitting blood flow between the plurality of wires and through the cardiac vessel, and
      wherein the anchor serves as a recording electrode;
   a plurality of electrodes that are disposed along the catheter shaft, wherein the anchor is disposed between a first set of electrodes and a second set of electrodes;
   a flexible elongate mandrel that extends within the catheter shaft and is coupled at one end to an actuator and at an opposite end to the collar, wherein the mandrel is configured to carry electrical signals from the anchor; and
   the actuator for causing deployment and collapsing of the plurality of wires within the cardiac vessel.

2. The catheter of claim 1, wherein the electrophysiology catheter comprises a coronary sinus catheter and the cardiac vessel comprises a coronary sinus.

3. The catheter of claim 1, wherein a second end of each of the plurality of wires is attached to the catheter shaft.

4. The catheter of claim 1, wherein the plurality of wires are electrically isolated from the plurality of electrodes that are disposed along the catheter shaft.

5. The catheter of claim 4, further comprising a plurality of separate electrical wires routed to the plurality of wires of the anchor.

6. The catheter of claim 5, wherein the plurality of wires are insulated from one another by an insulation coating.

7. The catheter of claim 1, wherein the actuator is a slide actuator disposed within the handle, wherein a sliding action of the actuator is translated through the mandrel to the collar.

8. The catheter of claim 7, further including an actuator lock mechanism for locking the actuator in first and second positions that correspond respectively to the anchor being in a fully deployed position and a fully collapsed as well as intermediate positions therebetween.

9. The catheter of claim 1, wherein the plurality of electrodes disposed along the catheter shaft are recording electrodes.

10. The catheter of claim 9, wherein the recording electrodes are configured to be operably connected to a recording device.

11. The catheter of claim 9, wherein the recording electrodes are configured to be operably connected to a 3D mapping system.

12. The catheter of claim 1, wherein the first set of electrodes are spaced a first distance from the second set of electrodes along the catheter shaft, and the first distance is maintained when the plurality of wires move between the deployed position and the collapsed position.

13. The catheter of claim 1, wherein catheter shaft extends distally of the anchor.

* * * * *